United States Patent

Wu et al.

[11] Patent Number: 5,073,560
[45] Date of Patent: Dec. 17, 1991

[54] SPIRO-ISOXAZOLIDINE DERIVATIVES AS CHOLINERGIC AGENTS

[75] Inventors: Edwin S. Wu; Alexander Kover, both of Rochester, N.Y.

[73] Assignee: Fisons Corporation, Rochester, N.Y.

[21] Appl. No.: 556,112

[22] Filed: Jul. 20, 1990

[51] Int. Cl.$^5$ .................... A61K 31/44; C07D 498/10
[52] U.S. Cl. ........................................ 514/278; 546/19
[58] Field of Search ........................... 546/19; 514/278

[56] References Cited

U.S. PATENT DOCUMENTS

| 4,735,944 | 4/1988 | Bolliger | 546/19 X |
| 4,940,795 | 7/1990 | Tsukamoto et al. | 546/16 |
| 4,962,083 | 10/1990 | Herman et al. | 501/123 |

FOREIGN PATENT DOCUMENTS 0311313  4/1989  European Pat. Off.
2-164882 6/1990  Japan.

OTHER PUBLICATIONS

Chemical Abstracts Service 113:211966j, 1990.
Abraham et al., *J. Chem. Soc.*, Perkin Trans. 2, (10), 1355-1375 (1989).
De Amici et al., *Europ. J. of Med. Chem.*, 24, 171-177 (1989).
Miles, *J. Amer. Chem. Soc.*, 79, 2565-2568 (1957).
Vyas et al., *Tet. Letts.*, 25, 487-490 (1984).

Primary Examiner—Catherine S. Kirby Scalzo
Attorney, Agent, or Firm—Tom A. Davidson

[57] ABSTRACT

Compounds of general formula I,

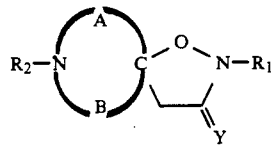

wherein:
A represents $(CH_2)_m$ optionally substituted by $R_3$,
B represents $(CH_2)_n$ optionally substituted by $R_4$,
$R_1$ represents hydrogen, $C_1$-$C_6$ alkyl, $C_{1-6}$ alkenyl or $C_{1-6}$ alkynyl,
$R_2$ represents hydrogen, $C_1$-$C_6$ alkyl or $COOR_5$, in which $R_5$ represents $C_1$-$C_6$ alkyl,
$R_3$ and $R_4$ independently represent hydrogen or $C_1$-$C_6$ alkyl,
in addition, any two of $R_2$, $R_3$ and $R_4$ may together form a $C_{1-3}$ alkylene chain,
n and m independently represent an integer from 1-3 inclusive,
Y represents O or S,
and pharmaceutically acceptable acid addition salts thereof are useful as pharmaceuticals, in particular as central muscarinic acetylcholine receptor agonists. The compounds are therefore useful in the treatment of diseases such as presenile and senile dementia, Huntington's chorea, tardive dyskinesia, hyperkinesia, mania and Tourette Syndrome.

8 Claims, No Drawings

SPIRO-ISOXAZOLIDINE DERIVATIVES AS CHOLINERGIC AGENTS

SUMMARY

This invention relates to novel chemical compounds, processes for their preparation, pharmaceutical compositions containing them, and methods of treatment involving their use. According to this invention, we provide novel spiroisoxazolidine derivatives of azacyclic amines which possess central cholinergic properties and thus are useful in the treatment of certain neurological disorders and mental illnesses.

BACKGROUND

According to the cholinergic hypothesis of memory impairment in Alzheimer's disease, senile dementia and age-associated memory impairment a deficiency of cholinergic function plays a major role in the progressive development of the disease. This has led to the belief that enhancement of muscarinic cholinergic transmissions at cerebal cortical sites would be beneficial for treatment of the disease. Arecoline, a piperidine derivative, and aceclidine, a quinuclidine derivative are both muscarinic agonists; however, they exhibit undesirable clinical effects and there is a need for derivatives with more desirable clinical profiles.

Spiro derivatives of quinuclidine and piperidine are known to have cholinergic properties. For example, European Patent Application 0311313 discloses spirofurane and spirotetrahydrothiophene derivatives of quinuclidine and piperidine. A spiroisoxazolidin-3-one derivative, 2-aza-1-oxaspiro[4,5]-decan-3-one is known [J. Chem. Soc., Perkin Trans. 2, (10), 1355(1989)] as a chemical intermediate but to the best of our knowledge is not known to have any cholinergic properties. De Amici et al [Europ. J. of Med. Chem. 24, 171-177(1989)] disclose isoxazolidin-3-one derivatives of muscarone with muscarinic activity.

DETAILED DESCRIPTION

According to the invention there are provided compounds of formula I,

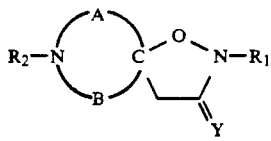

wherein:
A represents $(CH_2)_m$ optionally substituted by $R_3$,
B represents $(CH_2)_n$ optionally substituted by $R_4$,
$R_1$ represents hydrogen, $C_1$-$C_6$ alkyl, $C_1$-$C_6$ alkenyl or $C_1$-$C_6$ alkynyl,
$R_2$ represents hydrogen, $C_1$-$C_6$ alkyl or $COOR_5$, in which $R_5$ represents $C_1$-$C_6$ alkyl,
$R_3$ and $R_4$ independently represent hydrogen or $C_1$-$C_6$ alkyl,
in addition, any two of $R_2$, $R_3$ and $R_4$ may together form a $C_{1-3}$ alkylene chain,
n and m independently represent an integer from 1-3 inclusive,
Y represents O or S,
and pharmaceutically acceptable acid addition salts thereof.

Pharmaceutically acceptable acid addition salts of the compounds of formula I include the salts of mineral acids, for example, hydrochloric acid, sulphuric acid or phosphoric acid, and organic acids for example monobasic acids such as acetic acid or formic acid, and polybasic acids such as maleic acid, fumaric acid, succinic acid, etc. Salts may be readily formed from the compound of formula I by mixing with the appropriate acid or by exchange with an other acid addition salt of the compound of formula I.

Particular rings that A-N($R_2$)-B, together with the carbon atom to which they are attached (hereinafter "ring A"), may represent include:
piperidine,
1-azabicyclo[2.2.2]octane (known also as quinuclidine),
1-azabicyclo[3.2.2]nonane,
1-azabicyclo[3.3.1]nonane,
1-azabicyclo[3.1.1]heptane,
1-azabicyclo[2.2.1]heptane,
1-azabicyclo[3.2.1]octane,
6-azabicyclo[3.2.1]octane and,
8-azabicyclo[3.2.1]octane.

We prefer compounds, however, in which ring A represents piperidine, quinuclidine or 1-azabicyclo(2.2.1)-heptane.

Alkyl groups that $R_1$, $R_2$, $R_3$ and $R_4$ may represent include methyl, ethyl, n-propyl, iso-propyl, n-butyl, iso-butyl, s-butyl and t-butyl. We prefer compounds, however, in which the alkyl group is methyl or ethyl.

Alkenyl groups that $R_1$ may represent include allyl and 2-butenyl.

Alkynyl which $R_1$ may represent include propargyl and 2-butynyl.

We prefer compounds in which Y represents O.
We prefer compounds in which the sum of n+m is 4
We prefer compounds in which ring A is piperidine.
We prefer compounds in which $R_1$ is alkyl, especially methyl.
We prefer compounds in which $R_2$ is alkyl, especially methyl.

As a preferred group of compounds there are provided compounds of formula I, in which
A and B are independently $(CH_2)_2$, Y is O and $R_1$ and $R_2$ are $C_{1-6}$ alkyl.

Many of the compounds of the present invention have at least one asymmetric centre and can therefore exist as enantiomers, and in some cases as diastereomers. It is to be understood that the invention covers all such isomers and mixtures thereof.

According to this invention there is also provided a process for the preparation of compounds of formula I or pharmaceutically acceptable acid addition salts thereof which comprises a) preparing a compound of formula I in which $R_1$ represents other than hydrogen by thermal rearrangement of a corresponding compound of formula II,

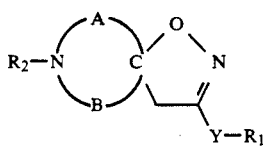

or b) preparing a compound of formula I in which $R_1$ represents hydrogen and Y represents O, by hydrolysis of a corresponding compound of formula III,

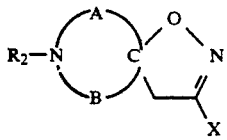

in which X represents a good leaving group and $R_2$, A and B are as defined above, or c) preparing a compound of formula I in which Y is S by thiation of a corresponding compound of formula I in which Y is O, and where desired or necessary converting the corresponding compound of formula I into a pharmaceutically acceptable acid addition salt thereof or vice versa.

In the reaction of process (a), methods similar to those described by Miles, H. T., [J Amer. Chem. Soc. 79,2565-8(1957)] may be used. The reaction may be carried out in the absence of a solvent and at a temperature of, for example, from 100°-250° C.

In the reaction of process (b) good leaving groups that X may represent include halide, for example bromide, and alkoxy, e.g. methoxy. The hydrolysis may be carried out in the presence of an acid, for example, hydrochloric or sulfuric acid in a solvent. Protic solvents are preferred, for example, methanol, ethanol or water or mixtures thereof and at a temperature of, for example, from 0°-100° C.

In process (c) the thiation reaction may be carried out by methods similar to those described by De Amici using, for example, 2,4-bis(4-methoxyphenyl)-1,3-dithia-2,4-diphosphetane-2,4-disulfide (Lawesson's Reagent) in an inert solvent, for example, toluene at a temperature of, for example, from 50°-120° C.

Compounds of formula II may be prepared by reacting the corresponding compound of formula III with a compound of formula IV,

$R_1YH$          IV in which $R_1$ and Y are as defined above.

The reaction may be carried out by heating the compound of formula III with the appropriate alcohol or thioalcohol in the presence of a base, for example, potassium carbonate. The reaction may be carried out at a temperature of, for example, from 20°-100° C.

Compounds of formula III may be prepared by reacting a corresponding compound of formula V,

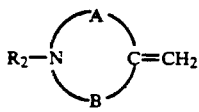

in which $R_2$, A and B are as defined above, with a nitrile oxide of formula VI,

X-C≡N-O          VI in which X is as defined above.

The nitrile oxide of formula VI may be prepared in situ from a compound of formula VII, $(X)_2C=N\text{-}OH$          VII by treatment with base. The reaction may be carried out by methods similar to those described by Vyas, D. M. et. al. [Tet. Letts. 25, 487–490(1984)]. The reaction may be carried out in the presence of a base, for example, sodium or potassium bicarbonate or sodium acetate in a suitable solvent. Suitable solvents include water or an aprotic solvent, for example, ethyl acetate or methylene chloride. The reaction may be carried out at a temperature of, for example, from −10°-30° C.

The starting material of formula V may be prepared by a number of methods, for example, by reacting the corresponding compound of formula VIII,

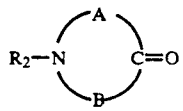

with a Wittig reagent, for example, methyl triphenylphosphonium bromide in the usual manner. The reaction may be carried out in the presence of a base, for example, butyl lithium, in an aprotic solvent, for example, THF or hexane or mixtures of solvents, at a temperature of, for example, from 0°-50° C.

Compounds of formula IV, VII and VIII are either known compounds which are commercially available or may be prepared by literature methods from compounds known per se.

The compounds of the present invention are useful because they possess pharmacological activity in animals. In particular, the compounds bind to central muscarinic acetylcholine receptors as can be demonstrated in studies of the affinity constants of the compounds for [$^3$H]-oxotremorine-M binding sites in rat cortical membrane preparations. The compounds may therefore be useful in the treatment of neurological and mental illnesses whose clinical manifestations are due to involvement of specific populations of cholinergic neurones. Such diseases include presenile and senile dementia (also known as Alzheimer's disease and senile dementia of the Alzheimer type respectively), Huntington's chorea, tardive dyskinesia, hyperkinesia, mania and Tourette Syndrome. The compounds are also useful analgesic agents and therefore useful in the treatment of severe painful conditions such as rheumatism, arthritis, and terminal illness.

In a procedure for measuring agonist efficacy at M1 muscarinic receptors in rat brain hippocampus the muscarinic cholinergic agonist activity of a test compound is measured using an in vitro M1 muscarinic receptor linked enzyme assay which measures the formation of inositol phosphate from phosphatidyl inositol. The assay procedure is described in detail by Fisher S. K. and Bartus R. T., J. Neurochem. 45: 1085-1095(1985). Rat brain hippocampal tissue was cross sliced into 350×350 um segments which were equilibrated for one hour at 37° C. in oxygenated Krebs-Hensleit buffer. Aliquots of slices were then incubated with [$^3$H]myoinositol, lithium chloride, and various concentrations of test compound for 120 minutes in a 95% $O_2$/5% $CO_2$ atmosphere at 37° C. The reaction is terminated by addition of chloroform/methanol solution (1:2, v/v) and the [$^3$H]inositol phosphates were extracted into the aqueous phase. [$^3$H]Inositol phosphates were purified by ion exchange chromatography using Dowex AG-1×8 anion exchange resin in the formate form. Inositol phosphates were selectively eluted from the resin with a 1 M ammonium formate 0.1 M formic acid solution. Tritium was determined by liquid scintillation spectroscopy. The magnitude of stimulation of inositol phosphate formation by high concentrations of full agonists such a carbachol was assigned a value of 100%. Partial agonists produced a maximal rate of inositol phosphate formation which varied, according to the compound, from 10 to 80%. Weak partial agonists and antagonists did not stimulate the formation of inositol phosphates.

Compounds of formula I with a maximal rate of inositol phosphate formation of greater than 15% are preferred.

Partial agonists identified in the above assays may be tested for any selectivity for M1 versus M2 receptors. A measure of M2-receptor mediated inhibition of adenylate cyclase in rat heart membranes can be obtained according to procedures described by Ehlert, F. J. et al. [J Pharmacol. Exp. Ther. 228:23–29(1987)]. Some of the compounds may possess muscarinic antagonist properties and thus may be useful as antisecretory agents in the management of peptic ulcers and acute rhinitis, or in the treatment of motion sickness and parkinsonism.

Thus, according to another aspect of the invention, there is provided a method of treatment of a neurological condition selected from the group consisting of presenile and senile dementia, Huntington's chorea, tardive dyskinesia, hyperkinesia, mania and Tourette Syndrome, which method comprises administering to a patient suffering from that condition a therapeutically effective quantity of one or more compounds of formula I.

The compounds of the invention may be administered by any convenient route, e.g. orally, parenterally or rectally. The daily dose required will of course vary with the particular compound used, the particular condition being treated and with the severity of that condition. However, in general a total daily dose of from about 0.1 to 10 mg/kg of body weight, preferably about 0.1 to 1 mg/kg is suitable, administered from 1 to 4 times a day.

For use in the method of treatment of the invention the compound of formula I will generally be administered in the form of a suitable pharmaceutical composition. Thus, according to another aspect of the invention, there is provided a pharmaceutical composition comprising a compound of formula I in admixture with a pharmaceutically acceptable carrier.

The pharmaceutical composition is preferably in unit dose form. Such forms include solid dosage forms, e.g. tablets, pills, capsules, powders, granules, and suppositories for oral, parenteral or rectal administration, and liquid dosage forms, e.g. sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid compositions may be prepared by mixing the active ingredient with pharmaceutical carriers, e.g. conventional tabletting ingredients such as corn starch, lactose, sucrose, sorbitol, talc, stearic acid, magnesium stearate, dicalcium phosphate, gums and other diluents, e.g. water, to form a homogeneous preformulation composition in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the composition.

In order to reduce unwanted peripherally mediated side effects, it may be advantageous to include in the composition a peripherally acting cholinergic antagonist (or anti-muscarinic agent) such as N-methylscopolamine, N-methylatropine, propantheline, methantheline or glycopyrrolate.

The compounds of the invention, together with their pharmaceutically acceptable acid addition salts, have advantageous properties in that they are more potent, more selective, less toxic, give rise to fewer side effects, have a longer duration of action, are more efficacious or have other advantageous pharmaceutical properties, compared to known compounds of similar structure.

The invention will now be illustrated, but in no way limited, by the following Examples in which all temperatures are in degrees Celsius, THF is tetrahydrofuran, MeOH is methanol, $CHCl_3$ is chloroform, EtOAc is ethyl acetate, $CH_2Cl_2$ methylene chloride and ether is diethyl ether.

EXAMPLES

Example 1

2,8-Dimethyl-1-oxa-2,8-diazaspiro[4,5]decan-3-one maleate.

a) 1Methyl-4-methylenepiperidine hydrochloride.

A solution of 2.5 M n-butyl lithium(80 mL, 0.2 mol) was added to a suspension of methyl triphenylphosphonium bromide in THF(600 mL) under a nitrogen atmosphere at room temperature. The mixture was stirred for 2.5 hours. A solution of 1-methyl-4-piperidinone(22.6 g, 0.2 mol) in THF(60 mL) was added dropwise and the suspension was stirred for 2 hours. The reaction was decomposed by the addition of water. The aqueous phase was saturated with NaCl and then the organic phase was separated. The aqeos phase was extracted with chloroform and the combined organic extracts were concentrated. The residual oil was dissolved in methanol and acidified with hydrogen chloride to give the title compound (16.87 g).

Similarly acidification of the amine with maleic acid afforded the title compound as the maleate salt.

b) 3-Bromo-8-methyl-1-oxa-2,8-diazaspiro[4,5]dec-2-ene

To a solution of 1-methyl-4-methlenepiperidine maleate (1.8 g, 0.0081 mol) in saturated sodium bicarbonate (50 mL) was added dibromoformaldoxime (4.94 g, 0.0244 mol) portionwise. The reaction was stirred at room temperature for 1.5 hours. Additional sodium carbonate was added and then the reaction mixture was extracted with chloroform. The extract was dried($MgSO_4$) and the solvent was evaporated. The residue was purified by flash chromatography on silica gel and elution with ammoniated $CHCl_3$/EtOAc/MeOH (2/2/1) to give an oil (0.67 g) which solidified. The solid was dissolved in ether and filtered from the insolubles. The filtrate was acidified with maleic acid and the precipitated solid was recrystallized from EtoAc/$Et_2O$ to give the bromo derivative as the maleate salt, mp. 159°–160.5° C.

c) 3-Methoxy-8-methyl-1-oxa-2,8-diazaspiro[4,5]dec-2-ene.

The bromo base from step (b) (0.2 g) and potassium carbonate (0.64 g) were suspended in MeOH (10 mL) and heated at reflux for 3 hours. Water was added and the aqueous layer was extracted with chloroform. The combined extracts were dried (MgSO$_4$) and concentrated to give the methyl ether as an oil which solidified.

d) 2,8-Dimethyl-1-oxa-2,8-diazaspiro[4,5]decan-3-one maleate.

3-Methoxy-8-methyl-1-oxa-2,8-diazaspiro[4,5]dec-2-ene (1.94 g) was heated at 200° C. for 2 hours under nitrogen. The reaction was cooled and the residue was chromatographed on ammoniated silica gel and eluted with CHCl$_3$/EtOAc/MeOH(2/2/1) to give a yellow oil (1.45 g). The oil was dissolved in ether and filtered from some insolubles. The ether solution was acidified with maleic acid and the precipitated solid was filtered and then recrystallised from CH$_2$Cl$_2$/EtOAc(1/1). The precipitated solid was filtered and dried to give the title compound (1.74 g), mp 153.5°–155° C.

We claim:

1. A compound of formula I,

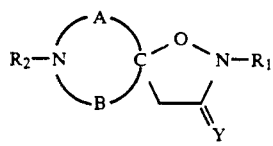

wherein:

A represents (CH$_2$)$_m$ optionally substituted by R$_3$,

B represents (CH$_2$)$_n$ optionally substituted by R$_4$,

R$_1$ represents hydrogen, C$_1$–C$_6$ alkyl, C$_{1-6}$ alkenyl or C$_{1-6}$ alkynyl, R$_2$ represents hydrogen, C$_1$–C$_6$ alkyl or COOR$_5$, in which R$_5$ represents C$_1$–C$_6$ alkyl, R$_3$ and R$_4$ independently represent hydrogen or C$_1$–C$_6$ alkyl, n and m independently represent an integer 2, Y represents O or S, and pharmaceutically acceptable acid addition salts thereof.

2. A compound according to claim 1, wherein Y represents O.

3. A compound according to claim 1, wherein R$_1$ and R$_2$ are independently represented by C$_{1-6}$ alkyl.

4. A compound according to claim 1, wherein R$_1$ is represented by methyl.

5. A compound according to claim 1, which is
2,8-Dimethyl-1-oxa-2,8-diazaspiro[4,5]decan-3-one
or a pharmaceutically acceptable acid addition salt thereof.

6. A compound according to claim 1 which is in the form of a pharmaceutically acceptable acid addition salt.

7. A method of treatment of a neurological condition selected from the group consisting of presenile and senile dementia, Huntington's chorea, tardive dyskinesia, hyperkinesia, mania and Tourette Syndrome, which method comprises administering to a patient suffering from that condition a therapeutically effective amount of one or more compounds of formula I, as defined in claim 1, or a pharmaceutically acceptable acid addition salt thereof.

8. A pharmaceutical composition comprising a compound of formula I, as defined in claim 1, or a pharmaceutically acceptable acid addition salt thereof in admixture with a pharmaceutically acceptable carrier, excipient or diluent.

* * * * *